US005811278A

United States Patent [19]

Okamura et al.

[11] Patent Number: 5,811,278
[45] Date of Patent: Sep. 22, 1998

[54] **DIPEPTIDYL PEPTIDASE IV FROM *XANTHOMONAS MALTOPHILIA* AND PROCESS FOR PRODUCING THE SAME**

[75] Inventors: Hideki Okamura; Jiro Kataoka, both of Kanagawa; Tadashi Yoshimoto, Nagasaki, all of Japan

[73] Assignee: Ajinomoto Co., Inc., Tokyo, Japan

[21] Appl. No.: 684,480

[22] Filed: Jul. 19, 1996

[30] Foreign Application Priority Data

Jul. 21, 1995 [JP] Japan .................................. 7-185811

[51] Int. Cl.$^6$ ............................... C12N 9/48; C12P 21/04
[52] U.S. Cl. ......................... 435/212; 435/71.1; 435/71.2
[58] Field of Search .................................. 435/212, 71.1, 435/71.2

[56] References Cited

FOREIGN PATENT DOCUMENTS

WO 94/16082   7/1994   WIPO .

OTHER PUBLICATIONS

Journal of Bacteriology, vol. 174, No. 8, pp. 2454–2459, Apr. 1992, E. Szwajcer–Dey, et al., "Proline–Specific Endopeptidases from Microbial Sources: Isolation of an Enzyme from a Xanthomonas sp".

Archives of Biochemistry and Biophysics, vol. 270, No. 1, pp. 255–266, 1989, Yamuna Dasarathy, et al., "A Peptidyl Dipeptidase–4 from *Pseudomonas maltophilia*: Purification and Properties".

Biochemical and Biophysical Research Communications, vol. 158, No. 1, pp. 45–51, Jan. 16, 1989, Joseph J. Lanzillo, et al., "Amino Acid Residues Essential for Catalysis by Peptidyl Dipeptidase–4 from *Pseudomonas maltophilia*".

International Journal of Systematic Bacteriology, vol. 33, No. 2, pp. 409–413, Apr. 1983, J. Swings, et al., "Transfer of *Pseudomonas maltophilia* Hugh 1981 to the Genus Xanthomonas as *Xanthomonas maltophilia* (Hugh 1981) Comb. Nov".

Bioscience Biotechnology and Biochemistry, vol. 59, No. 11, pp. 2087–2090, Koushirou Suga, et al., "Prolidase from *Xanthomonas maltophilia*: Purification and Characterization of the Enzyme".

Kabashima et al. (1996) *J. Biochem.*, 120(6), "Dipeptidyl Peptidase IV from *Xanthomonas maltophilia*: Sequencing and Expression of the Enzyme Gene and Characterization of the Expressed Enzyme", pp. 1111–1117.

T. Yoshimoto et al. J. Biochem. vol. 91, No. 6, 1982; pp. 1899–1906, "Proline–Specific Dipeptidyl Aminopeptidase from *Flavobacterium meningosepticum*[1]".

K. Fukasawa et al. Archives Of Biochemistry and Biophysics, vol. 210, No. 1, Aug. 1981; pp. 230–237. "Purification and Properties of Dipeptidyl Peptidase IV from *Streptococcus mitis* ATCC 9811".

*Primary Examiner*—Jon P. Weber
*Attorney, Agent, or Firm*—Oblon, Spivak, McClelland, Maier & Neustadt, P.C.

[57] ABSTRACT

Dipeptidyl peptidase IV obtainable from a microorganism of the species *Xanthomonas maltophilia* is described, which hydrolyzes specifically a peptide and derivatives thereof having proline at the second position from the amino terminus to release a dipeptide having proline at the carboxyl terminus. Also, the process for producing the dipeptidyl peptidase IV is described.

8 Claims, No Drawings

DIPEPTIDYL PEPTIDASE IV FROM *XANTHOMONAS MALTOPHILIA* AND PROCESS FOR PRODUCING THE SAME

FIELD OF THE INVENTION

The present invention relates to novel dipeptidyl peptidase IV obtainable from a microorganism. Furthermore, the present invention relates to a process for producing it.

BACKGROUND OF THE INVENTION

Various types of dipeptidyl peptidase IV have been purified and the enzymological properties have been revealed. For example, the dipeptidyl peptidase IV is isolated from rat liver (Hopsu-Havu, V. K. & Glenner, G. G., *Histochem.*, 7:197–201 (1966)), swine kidney (Barth, A., Schulz, H. & Neubert, K., *Acta Biol. Med. Chem.*, 32:157–174 (1974)), small intestine (Svensson, B., Danielsen, M., Staun, M, Jeppesen, L., Noren, O. and Sjostrom, H., *Eur. J. Biochem.*, 90:489–498 (1978)), liver (Fukasawa, K. M., Fukasawa, K., Hiraoka, B. Y. & Harada, M., *Biochim. Biophys. Acta*, 657:179–189 (1981)), human submaxillary gland (Oya, H., Nagatsu, I. & Nagatsu, T., *Biochim. Biophys. Acta*, 258:591–599 (1972)), sheep kidney (Yoshimoto, T. & Walter, R., *Biochim. Biophys. Acta*, 485:391–401 (1977), Yoshimoto, T., Fischl, R. C., Orlowski, R. C. & Walter, R., *J. Biol. Chem.*, 253:3708–3716 (1978)) or microorganisms (Fukusawa, K. M. & Harada, M., *Arch. Biochem. Biophys.*, 210:230–237 (1981), Yoshimoto, T. & Tsuru, D., *J. Biochem.*, 91:1899–1906 (1982)).

The molecular weight of dipeptidyl peptidase IV is reported to be 230,000 to 250,000 in mammals. Also, in microorganisms, it is reported to be 120,000 in *Streptococcus mitis* and 160,000 in *Flavobacterium meningosepticum*.

Furthermore, the isoelectric point is reported to be about 4.7 in mammals. Also, in microorganisms, it is reported to be 4.0 in *Streptococcus mitis* and 9.5 in *Flavobacterium meningosepticum*.

With regard to the thermal stability, the dipeptidyl peptidase IV in sheep kidney is stable up to 70° C. and completely inactivated at 80° C. Among microorganisms which can produce an enzyme in a large quantity, the dipeptidyl dipeptidase IV in *Streptococcus mitis* is comparatively stable up to 50° C. but completely inactivated at 55° C. Consequently, microbial contamination may be occurred when produced on an industrial scale.

On the other hand, the dipeptidyl dipeptidase IV in *Flavobacterium meningosepticum* is comparatively stable up to 50° C. and maintains 50% of the activity even at 55° C. Consequently, it has an advantage in that there is no danger of causing microbial contamination during the enzyme reaction when used on an industrial scale.

The optimum pH of dipeptidyl peptidase IV is pH 8.7 in mammals and pH 7.4 to 7.8 in *Flavobacterium meningosepticum*, thus having a considerably narrow range. On the other hand, the optimum pH of dipeptidyl peptidase IV in *Streptococcus mitis* has a broad range of pH 6.0 to 8.7, and therefore, it seems to have high applicability.

An aminopeptidase having broad substrate specificity such as leucine aminopeptidase hydrolyzes a peptide in sequence from the amino terminus to release an amino acid. However, the hydrolysis is terminated when an amino acid residue followed by proline is reached. As a result, a peptide having a bond of X-Pro-Y- (X and Y are optional amino acids) remains.

Consequently, discovery of dipeptidyl peptidase IV capable of releasing X-Pro which is a substrate of prolidase (proline dipeptidase) will render possible high degree hydrolysis of protein and its broad application. Thus, great concern has been directed toward the isolation of dipeptidyl peptidase IV from bacteria from which a large quantity of the enzyme can be prepared comparatively easily.

However, as described above, nothing has been reported on bacterial dipeptidyl peptidase IV having both a comparatively high thermal stability effective for preventing microbial contamination during the enzyme reaction on an industrial scale and a broad optimum pH range effective for increasing the applicability.

SUMMARY OF THE INVENTION

Therefore, an object of the present invention is to provide a large quantity of bacterial dipeptidyl peptidase IV which has both properties of a comparatively high thermal stability and a broad optimum pH range.

This and other objects of the present invention have been attained by dipeptidyl peptidase IV obtainable from a microorganism of the genus Xanthomonas, which hydrolyzes specifically a peptide and derivatives thereof having proline at the second position from the amino terminus to release a dipeptide having proline at the carboxyl terminus.

Furthermore, this and other objects of the present invention have been attained by a process for producing dipeptidyl peptidase IV obtainable from a microorganism of the genus Xanthomonas, which comprises culturing said microorganism in a medium to produce and accumulate said dipeptidyl peptidase IV in the medium, and collecting the produced and accumulated dipeptidyl peptidase IV.

DETAILED DESCRIPTION OF THE INVENTION

The present inventors of the present invention have found that a dipeptidyl peptidase IV activity which shows both properties of a comparatively high thermal stability and a broad optimum pH range is present in a microorganism of the genus Xanthomonas already isolated as a prolidase-active bacterium that can hydrolyze Gly-Pro, and the present invention has been accomplished by revealing the various enzymatic characteristics of the dipeptidyl peptidase IV and establishing the preparation method.

Accordingly, the present invention relates to dipeptidyl peptidase IV which is obtainable from a microorganism of the genus Xanthomonas isolated by screening and which has the following characteristics.

The microorganism for use in the present invention preferably belongs to Xanthomonas maltophilia or a mutant thereof, and is more preferably *Xanthomonas maltophilia* AJ 13127 (Deposit No. FERM BP-5568) or a mutant thereof.

The dipeptidyl peptidase IV of the present invention (hereinafter often referred to as "the enzyme of the present invention") has the following characteristics.

(1) Action:

Within a pH range of 6.0 to 10.5, it acts on specifically a peptide having proline or alanine at the second position from the amino terminus to release a dipeptide having proline or alanine at the carboxyl terminus by hydrolyzing the peptide bond.

(2) Substrate specificity:

It shows an ability to hydrolyze a peptide and derivatives thereof having proline or alanine at the second position from the amino terminus.

(3) Optimum pH:

It shows an optimum pH of 6.0 to 10.0 when Gly-Pro-β-naphthylamide or Gly-Pro-p-nitroanilide is used as the substrate.

(4) Stable pH range:

It is stable within a pH range of from 7.0 to 9.0.

(5) Optimum reaction temperature:

The optimum temperature is 40° to 60° C. when Gly-Pro-β-naphthylamide or Gly-Pro-p-nitroanilide is used as the substrate.

(6) Stable temperature range:

It is stable within a range of about 35° to 55° C.

(7) Inhibitor:

The activity is inhibited by diisopropyl phosphofluoridate.

(8) Molecular weight:

The molecular weight is 150,000 to 170,000 measured by gel filtration and 75,000 to 90,000 measured by SDS-polyacrylamide gel electrophoresis.

(9) Effect of metal ions:

The activity is inhibited by $HgCl_2$.

Furthermore, the process for producing dipeptidyl peptidase IV in the present invention is described below in detail.

Using a plate medium prepared by adding agar to normal bouillon medium (produced by Kyokuto Pharmaceutical Industry Co., Ltd.) to give a final concentration of 2%, highly prolidase-active strains of various microorganisms from natural resources were obtained. The present inventors found that a microorganism of the genus Xanthomonas can produce and accumulate prolidase. When dipeptidyl peptidase IV activity of the microorganism was measured at the same time, the desired dipeptidyl peptidase IV was also found.

In the present invention, the dipeptidyl peptidase IV activity was measured according to the method of Yoshimoto et al. (*J. Biochem.*, 91:1899–1906 (1982)).

The nutrient medium used for culturing the microorganism of the genus Xanthomonas is a usual medium which comprises a carbon source, a nitrogen source, inorganic salts, auxiliary factors and the like. Examples of the carbon source include glucose, maltose, fructose, sucrose, lactose, starch and so on. They may be used alone or as a mixture thereof.

Examples of the nitrogen source include peptone, yeast extract, ammonium sulfate, casein, insoluble collagen, soybean protein and so on. Examples of the inorganic salts include sodium chloride, magnesium sulfate hepta-hydrate, disodium hydrogenphosphate, potassium dihydrogenphosphate and so on. Examples of the auxiliary factors include beef extract, corn steep liquor and so on.

Of these components, a medium containing 1% of beef extract, 1% of polypeptone and 0.5% of NaCl (pH 7.0) may be preferably used.

Culturing of dipeptidyl peptidase IV-producing microorganism in the present invention may be carried out under usual aerobic conditions at a medium pH of 6.0 to 8.0, preferably 6.5 to 7.5, at a temperature of 20° to 45° C., preferably 30° to 35° C., and for a period of 10 to 36 hours, preferably 12 to 25 hours.

The resulting culture mixture can be used as a dipeptidyl peptidase IV source as it is; however, specific activity of the dipeptidyl peptidase IV markedly increases and the stability is also improved when the dipeptidyl dipeptidase IV is separated and collected by the process of the present invention.

Furthermore, the dipeptidyl peptidase IV of the present invention is not limited to the enzyme produced by the process of the present invention, and it can be produced by means of recombinant DNA techniques using a recombinant strain of *Escherichia coli, Bacillus subtilis,* yeast or the like which is prepared by inserting the gene of the enzyme of the present invention into an expression vector and introducing the resulting vector into cells of the strain. The enzyme produced by either method will exert similar effects. Also, the process for purifying the enzyme is not limited and can be effected by combining usually used ion exchange chromatography, gel filtration and the like.

In the present invention, a dipeptidyl peptidase IV-producing microorganism may be subjected to an appropriate mutation treatment, such as exposure to ultraviolet light, X-ray or radiation, and a chemical treatment with a mutagenic compound (e.g., nitrsoguanidine, acridine dye). The thus obtained mutants can be used in the present invention as far as they are capable of producing the dipeptidyl peptidase IV of the present invention.

The present invention is now illustrated in greater detail by way of the following examples, but it should be understood that the present invention is not to be construed as being limited thereto.

EXAMPLE 1

Isolation of *Xanthomonas maltophilia* AJ 13127 (FERM BP-5568):

According to the usual method, a soil sample suspended in sterile water was spread on a plate medium (pH 7.0) which had been prepared by adding agar to normal bouillon medium (produced by Kyokuto Pharmaceutical Industry Co., Ltd.) to give a final concentration of 2%, and incubated at 30° C. to form about 500 colonies.

These colonies were inoculated into wells of 96 well plates and cultured to measure prolidase activity. As a result, a strain, KS-3, which showed prolidase activity was obtained. When the dipeptidyl peptidase IV activity was measured on the basis of an assumption that a microorganism having prolidase activity would also have dipeptidyl peptidase IV activity capable of providing a substrate of the prolidase, it was confirmed that the strain had the dipeptidyl peptidase IV activity. This strain, *Xanthomonas maltophilia* AJ 13127, has been internationally deposited in National Institute of Bioscience and Human Technology, Agency of Industrial Science and Technology. It has been assigned the designation as FERM BP-5568 (FERM P-14986).

Bacteriological characteristics of the strain are shown below.

(a) Morphological characteristics:

(1) Size and shape of cell:

Rod-shaped cell having a size of 0.4–0.5×1.0–1.5 μm (no pleomorphism).

(2) Gram stain:

Gram-negative.

(3) Motility:

Motile at 30° to 37° C.

(4) Flagella:

Polar flagella, plurality (1 to 3).

(b) Growth conditions on a nutrient medium:

(1) Nutrient agar plate medium:

Medium growth of circular and smooth colonies having luster. When the cells were suspended in physiological saline (0.9%), they were not able to be dispersed uniformly.

(2) Nutrient liquid medium:

Medium growth, forming an aggregated zone (1 mm in width) on the margin of liquid surface in the test tube. The broth became uniformly turbid, and formed viscous precipitate (2 days after culturing at 30° C.).

(3) McConkey agar plate medium:

Medium growth (30° or 37° C.) of circular and smooth colonies having luster. Color tone of the colony was semitransparent light yellow, and the periphery was orange. One of the control strains, *Xanthomonas maltophilia* ATCC 13637, did not grow on this medium.

(4) Tryptic Soy agar plate medium:

Medium growth at 30° C. The colony was circular and smooth and had luster. Color tone of the colony was light yellowish brown, and the periphery was semitransparent. All of the control strains of the *Xanthomonas maltophilia* AJ 2082, 2220 and 2554 showed closely similar appearances to those of the strain of the present invention. These strains were able to grow on this medium when 3% of sodium chloride was added, but their growth was inhibited when 10% of the salt was added (30° C.).

(c) Preservation conditions:

(1) Tryptic Soy agar slant medium:

This strain was able to be preserved for 1 month at 8° C., but cells on the slant medium became extinct after 6 months of preservation.

(2) Vacuum freeze drying:

The strain was able to be preserved at 15° C. for 18 years.

(3) Preservation at −80° C.:

One month of preservation was achieved under frozen condition in Tryptic Soy liquid medium (supplemented with 8% of DMSO).

(d) Physiological properties:

(1) Aerobic bacterium, so that no anaerobic growth.

(2) Growth temperature:

Growth (+) at 30° and 37° C., growth (−) at 41° C.

(3) Oxidase:

positive (+).

(4) Utilization of nitrate:

Negative (−). This strain did not use $KNO_3$ as the N source.

(5) Urease:

Negative (−).

(6) Decarboxylase:

Lysine decarboxylase (+), arginine decarboxylase (−), ornithine decarboxylase (−).

(7) Protease:

Casein hydrolysis (+), gelatin hydrolysis (−).

(8) Lipase activity:

Positive (+). An ability to hydrolyze Tween 80 was observed.

(9) Acid formation from sugars (30° C.):

The following results were obtained using an ammonium medium supplemented with respective sugars: glucose (−), cellobiose (−), maltose (+), fructose (−), arabinose (−), glycerol (−), lactose (−), trehalose (−), xylose (−).

(10) Assimilation of sugars (30° C.):

The following results were obtained using an ammonium medium and a minimum medium supplemented with respective sugars: glucose (+), cellobiose (+), maltose (+), lactose (+), trehalose (+).

(11) Hydrolysis of starch:

Negative (−).

(12) ONPG test:

Positive (+) (at 30° C.), negative (−) (at 37° C.).

(13) Utilization of citric acid:

Negative (−) (Simmon's citrate medium).

(14) Methionine requirement:

L-Met requirement was observed both in plate and liquid media. All of the control strains of *Xanthomonas maltophilia* (AJ 2082, 2220 and 2554) also showed L-Met requirement (liquid medium).

(15) Indole formation:

Negative (−) (30° and 37° C.).

(e) Production of yellow pigment:

Presence of a yellow pigment in the cells was confirmed. This pigment did not show the two absorption maxima at 425 to 475 nm reported in xanthomonasin.

(f) Ouinone type:

Ubiquinone (+), menaquinone (−).

(g) Analysis of cellular fatty acid composition:

Branched chain fatty acids were detected. Iso- and anteiso-type C15:0 fatty acids were found as characteristic fatty acids.

When taxonomic position of this strain was examined by referring these bacteriological characteristics to Bergey's Manual of Systematic Bacteriology (1984), International Journal of Systematic Bacteriology (1973) and Identification Methods in Applied and Environmental Microbiology vol.129 (1992), it was identified that this strain was a bacterium belonging to *Xanthomonas maltophilia*.

EXAMPLE 2

Preparation and characteristics of dipeptidyl peptidase IV obtainable from *Xanthomonas maltophilia*:

The thus obtained *Xanthomonas maltophilia* AJ 13127 FERM BP-5568 was inoculated into a medium containing 1% of beef extract, 1% of polypeptone and 0.5% of NaCl (pH 7.0) and pre-cultured at 30° C. for 24 hours to prepare a seed culture which was subsequently inoculated (1%) into a production medium and cultured at 30° C. for 12 hours. Thereafter, 12 liters of the thus obtained culture broth was centrifuged at 8,000 rpm for 30 minutes to obtain cells containing dipeptidyl peptidase IV.

The thus obtained cells were washed twice with 0.1M Tris-HCl buffer (pH 8.0) containing 5 mM EDTA, suspended in 20 mM Tris-HCl buffer (pH 8.0) containing 0.1% SDS and 5 mM EDTA and then disrupted using Dyno-Mill. The disrupted cells were centrifuged at 8,000 rpm for 30 minutes, ammonium sulfate was added to the resulting supernatant to a concentration of 40% saturation and the resulting mixture was centrifuged at 8,000 rpm for 30 minutes. The thus obtained supernatant was applied to a column packed with Toyopearl-HW65C which has been equilibrated in advance with 20 mM Tris-HCl buffer (pH 8.0) containing 40% ammonium sulfate and 5 mM EDTA. Fractions of dipeptidyl peptidase IV eluted by continuously reducing density of ammonium sulfate from 40% to 0% were pooled, mixed with 80% saturation of ammonium sulfate and then centrifuged at 8,000 rpm for 30 minutes. The thus obtained precipitate was dissolved in 20 mM Tris-HCl buffer (pH 8.0) containing 5 mM EDTA, and the solution was subjected to desalting using a Sephadex G-25 column and then applied to a column packed with DEAE-Toyopearl 650C which had been equilibrated in advance with the same buffer. Unabsorbed active fractions were pooled, concentrated using an ultrafiltration membrane and then applied to a column packed with hydroxylapatite which has been equilibrated in advance with 10 mM potassium phosphate buffer (pH 8.0). Elution was carried out by 10 mM to 500 mM density gradient of phosphate buffer (pH 8.0) to obtain purified dipeptidyl peptidase IV. Next, various enzymatic characteristics of the thus purified prolidase were examined.

Properties of the isolated novel dipeptidyl peptidase IV of the present invention are as follows.

(1) Action:

Within a pH range of 6.0 to 10.5, it acted on specifically a peptide having proline or alanine at the second position from the amino terminus to release a dipeptide having proline or alanine at the carboxyl terminus by hydrolyzing the peptide bond.

(2) Substrate specificity:

Table 1 shows the substrate specificity when low molecular weight synthetic substrates were used. The used substrates are shown in Table 1, and the concentration thereof was 0.5 mM.

The results in Table 1 show an ability to hydrolyze a peptide and derivatives thereof having proline or alanine at the second position from the amino terminus.

TABLE 1

Substrate specificity for peptide substrates

| Substrate | Relative activity (%) |
|---|---|
| Gly—Pro-β-naphthylamide | 100 |
| Ala—Pro-β-naphthylamide | 105 |
| Gly—Pro—Leu—Gly | 50 |
| Gly—Pro—Ala | 40 |
| Ala—Ala-β-naphthylamide | 100 |

(3) Optimum pH:

It showed an optimum pH of 6.0 to 10.0 when Gly-Pro-β-naphthylamide or Gly-Pro-p-nitroanilide was used as the substrate.

(4) Stable pH range:

It was stable within a pH range of from 7.0 to 9.0.

(5) Optimum reaction temperature:

The optimum temperature was 40° to 60° C. when Gly-Pro-β-naphthylamide or Gly-Pro-p-nitroanilide was used as the substrate.

(6) Temperature stability:

When it was incubated at pH 8.0 by varying the incubation temperature and then the residual activity was measured using Gly-Pro-β-naphthylamide as the substrate, 50% residual activity was found within a temperature range of about from 35° to 55° C.

(7) Influence of metal ions:

Influence of metal ions when Gly-Pro-β-naphthylamide was used as the substrate of the enzyme of the present invention is shown in Table 2. All of the used metals were 1 mM $HgCl_2$, $NiCl_2$ and $ZnCl_2$. The results in Table 2 show that the activity of the enzyme of the present invention is inhibited by $HgCl_2$ almost completely.

TABLE 2

Effect of metal ions on the activity

| Metal ion | Relative activity (%) |
|---|---|
| Control | 100 |
| $HgCl_2$ | 0 |
| $NiCl_2$ | 100 |
| $ZnCl_2$ | 95 |

(8) Inhibitor:

Relative activity of the enzyme of the present invention in the presence of each protease inhibitor was measured using Gly-Pro-β-naphthylamide as the substrate. The results are shown in Table 3. The results in Table 3 show that the activity of the enzyme of the present invention is inhibited almost completely by diisopropyl phosphofluoridate.

TABLE 3

Effect of chemical and peptide inhibitors

| Reagents | Concentration (mM) | Relative activity (%) |
|---|---|---|
| Control | | 100 |
| Diisopropyl phosphofluoridate | 1.0 | 0 |
| PCMB | 1.0 | 96 |
| EDTA | 5.0 | 100 |

(9) Molecular weight:

The molecular weight was 150,000 to 170,000 measured by gel filtration and 75,000 to 90,000 measured by SDS-polyacrylamide gel electrophoresis.

(10) Measurement of activity:

Using Gly-Pro-β-naphthylamide as the substrate, 0.1 ml of 5 mM Gly-Pro-β-naphthylamide and 0.1 ml of an enzyme solution were added to 0.8 ml of 20 mM Tris-HCl buffer (pH 8.0) containing 5 mM EDTA and allowed to react with each other at 37° C. for 5 minutes, the reaction was terminated by adding 0.5 ml of Fast Garnet GBC (0.1% solution prepared by dissolving it in 1M acetate buffer (pH 4.0) containing 10% Triton X-100) and then absorbance at 550 nm was measured.

As discussed above, the novel dipeptidyl peptidase IV of the present invention is an enzyme which can be obtainable efficiently from a microorganism of the genus Xanthomonas not reported in the prior art and is markedly useful from the industrial point of view because of the properties of both a high thermal stability and a broad optimum pH range which cannot be found in known bacterial dipeptidyl peptidase IV.

Consequently, the enzyme of the present invention will find versatile use in such applications as efficient hydrolysis and efficient use of protein by using prolidase or other enzymes in combination.

While the invention has been described in detail and with reference to specific embodiments thereof, it will be apparent to one skilled in the art that various changes and modifications can be made therein without departing from the spirit and scope thereof.

What is claimed is:

1. A purified dipeptidyl peptidase IV obtained from a microorganism of the species *Xanthomonas maltophilia*, which hydrolyzes specifically a peptide and derivatives thereof having proline at the second position from the amino terminus to release a dipeptide having proline at the carboxyl terminus.

2. The dipeptidyl peptidase IV as claimed in claim 1, wherein said dipeptidyl peptidase IV further hydrolyzes specifically a peptide and derivatives thereof having alanine at the second position from the amino terminus to release a dipeptide having alanine at the carboxyl terminus.

3. The dipeptidyl peptidase IV as claimed in claim 1, wherein said microorganism is *Xanthomonas maltophilia* AJ 13127 (Deposit No. FERM BP-5568).

4. The dipeptidyl peptidase IV as claimed in claim 1, which hydrolyzes said peptide and derivatives thereof at a pH of 6.0 to 10.5.

5. The dipeptidyl peptidase IV as claimed in claim 1, which is stable at a pH of 7.0 to 9.0.

6. The dipeptidyl peptidase IV as claimed in claim 1, which is stable at a temperature of 35° to 55° C.

7. A process for producing dipeptidyl peptidase IV obtained from a microorganism of the species *Xanthomonas maltophilia*, which comprises culturing said microorganism in a medium to produce and accumulate said dipeptidyl peptidase IV in the medium, and collecting the produced and accumulated dipeptidyl peptidase IV.

8. The process as claimed in claim 7, wherein said microorganism is *Xanthomonas maltophilia* AJ 13127 (Deposit No. FERM BP-5568).

* * * * *